US012636161B2

(12) United States Patent
Hessler et al.

(10) Patent No.: US 12,636,161 B2
(45) Date of Patent: May 26, 2026

(54) EXPANDING INTERVERTEBRAL IMPLANTS

(71) Applicant: GLOBUS MEDICAL, INC., Audubon, PA (US)

(72) Inventors: Tyler Hessler, Phoenixville, PA (US); Chad Glerum, Pennsburg, PA (US); Mark Weiman, Downingtown, PA (US); Albert Hill, Richboro, PA (US); Myles Sullivan, Philadelphia, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 18/822,801

(22) Filed: Sep. 3, 2024

(65) Prior Publication Data

US 2024/0423810 A1     Dec. 26, 2024

Related U.S. Application Data

(63) Continuation of application No. 17/699,752, filed on Mar. 21, 2022, now Pat. No. 12,076,250, which is a continuation of application No. 16/902,921, filed on Jun. 16, 2020, now Pat. No. 11,298,240.

(51) Int. Cl.
| | |
|---|---|
| *A61F 2/44* | (2006.01) |
| *A61F 2/30* | (2006.01) |
| *A61F 2/46* | (2006.01) |

(52) U.S. Cl.
CPC .......... *A61F 2/4425* (2013.01); *A61F 2/4611* (2013.01); *A61F 2002/3008* (2013.01); *A61F 2002/30411* (2013.01); *A61F 2002/30538* (2013.01); *A61F 2002/30556* (2013.01); *A61F 2002/443* (2013.01); *A61F 2002/4615* (2013.01)

(58) Field of Classification Search
CPC   A61F 2/4611; A61F 2002/443; A61F 2/4455; A61F 2/4425; A61B 17/1635
See application file for complete search history.

(56) References Cited

U.S. PATENT DOCUMENTS

| | | | |
|---|---|---|---|
| 4,349,921 | A | 9/1982 | Kuntz |
| 4,599,086 | A | 7/1986 | Doty |
| 4,863,476 | A | 9/1989 | Shepperd |
| 4,863,477 | A | 9/1989 | Monson |

(Continued)

FOREIGN PATENT DOCUMENTS

| | | |
|---|---|---|
| CA | 2088066 A1 | 1/1992 |
| DE | 4012622 C1 | 7/1991 |

(Continued)

*Primary Examiner* — Matthew J Lawson

(57)     ABSTRACT

A spacer separates bones of a joint using a driver tool having a threaded shaft. The spacer has a superior endplate with inferior facing ramps, and an inferior endplate with superior facing ramps. Two bearings are positioned between the endplates, each bearing has superior facing ramps which mate with the inferior facing ramps of the superior endplate, and inferior facing ramps which mate with the superior facing ramps of the inferior endplate. One bearing has a threaded aperture, and the other a thrust surface. A threaded shaft is threaded into the threaded aperture to push against the thrust surface to drive the bearings apart. As the bearings move apart, the mated ramps slide against each other to drive the superior and inferior endplates apart.

15 Claims, 7 Drawing Sheets

(56)                    References Cited

U.S. PATENT DOCUMENTS

| | | | |
|---|---|---|---|
| 5,123,926 A | 6/1992 | Pisharodi | |
| 5,290,312 A | 3/1994 | Kojimoto et al. | |
| 5,306,310 A | 4/1994 | Siebels | |
| 5,375,823 A | 12/1994 | Navas | |
| 5,390,683 A | 2/1995 | Pisharodi | |
| 5,522,899 A | 6/1996 | Michelson | |
| 5,534,030 A | 7/1996 | Navarro et al. | |
| 5,554,191 A | 9/1996 | Lahille et al. | |
| 5,571,192 A | 11/1996 | Schonhoffer | |
| 5,645,596 A | 7/1997 | Kim | |
| 5,653,763 A | 8/1997 | Errico et al. | |
| 5,665,122 A | 9/1997 | Kambin | |
| 5,676,701 A | 10/1997 | Yuan et al. | |
| 6,039,761 A | 3/2000 | Li et al. | |
| 6,045,579 A | 4/2000 | Hochschuler et al. | |
| 6,080,193 A | 6/2000 | Hochschuler et al. | |
| 6,099,531 A | 8/2000 | Bonutti | |
| 6,126,689 A | 10/2000 | Brett | |
| 6,176,882 B1 | 1/2001 | Biedermann et al. | |
| 6,258,125 B1 | 7/2001 | Paul et al. | |
| 6,554,863 B2 | 4/2003 | Paul et al. | |
| 6,558,423 B1 | 5/2003 | Michelson | |
| 6,562,074 B2 | 5/2003 | Gerbec et al. | |
| 6,576,016 B1 | 6/2003 | Hochschuler et al. | |
| 6,641,614 B1 | 11/2003 | Wagner et al. | |
| 6,648,917 B2 | 11/2003 | Gerbec et al. | |
| 6,666,891 B2 | 12/2003 | Boehm, Jr. et al. | |
| 6,692,495 B1 | 2/2004 | Zacouto | |
| 6,706,070 B1 | 3/2004 | Wagner et al. | |
| 6,752,832 B2 | 6/2004 | Ulrich | |
| 6,814,756 B1 | 11/2004 | Michelson | |
| 6,830,589 B2 | 12/2004 | Erickson | |
| 6,849,093 B2 | 2/2005 | Michelson | |
| 6,852,129 B2 | 2/2005 | Gerbec et al. | |
| 6,863,673 B2 | 3/2005 | Gerbec et al. | |
| 6,881,228 B2 | 4/2005 | Zdeblick et al. | |
| 7,018,415 B1 | 3/2006 | McKay | |
| 7,070,598 B2 | 7/2006 | Lim et al. | |
| 7,204,853 B2 | 4/2007 | Gordon | |
| 7,217,291 B2 | 5/2007 | Zucherman et al. | |
| 7,282,063 B2 | 10/2007 | Cohen et al. | |
| 7,316,714 B2 | 1/2008 | Gordon | |
| 7,473,276 B2 | 1/2009 | Aebi et al. | |
| 7,547,325 B2 | 6/2009 | Biedermann et al. | |
| 7,621,953 B2 | 11/2009 | Braddock, Jr. et al. | |
| 7,641,693 B2 | 1/2010 | Gutlin et al. | |
| 7,682,396 B2 | 3/2010 | Beaurain et al. | |
| 7,749,270 B2 | 7/2010 | Peterman | |
| 7,753,958 B2 | 7/2010 | Gordon | |
| 7,771,473 B2 | 8/2010 | Thramann | |
| 7,780,732 B2 | 8/2010 | Abernathie | |
| 7,799,081 B2 | 9/2010 | McKinley | |
| 7,815,683 B2 | 10/2010 | Melkent et al. | |
| 7,837,734 B2 | 11/2010 | Zucherman et al. | |
| 7,875,078 B2 | 1/2011 | Wysocki et al. | |
| 7,901,409 B2 | 3/2011 | Canaveral et al. | |
| 7,909,869 B2 | 3/2011 | Gordon | |
| 7,951,199 B2 | 5/2011 | Miller | |
| 7,985,256 B2 | 7/2011 | Grotz et al. | |
| 8,062,375 B2 | 11/2011 | Glerum | |
| 8,070,813 B2 | 12/2011 | Grotz et al. | |
| 8,123,810 B2 | 2/2012 | Gordon | |
| 8,137,405 B2 | 3/2012 | Kostuik et al. | |
| 8,192,495 B2 | 6/2012 | Simpson et al. | |
| 8,303,663 B2 | 11/2012 | Jimenez et al. | |
| 8,377,140 B2 | 2/2013 | DeFalco et al. | |
| 8,394,129 B2 | 3/2013 | Lopez et al. | |
| 8,394,143 B2 | 3/2013 | Grotz et al. | |
| 8,435,296 B2 | 5/2013 | Kadaba et al. | |
| 8,454,695 B2 | 6/2013 | Grotz et al. | |
| 8,647,386 B2 | 2/2014 | Gordon | |
| 8,696,751 B2 | 4/2014 | Ashley et al. | |
| 8,771,360 B2 | 7/2014 | Jimenez et al. | |
| 8,894,710 B2 | 11/2014 | Simpson et al. | |
| 8,932,355 B2 | 1/2015 | Grotz et al. | |
| 8,940,049 B1 | 1/2015 | JImenez et al. | |
| 8,956,413 B2 | 2/2015 | Ashley et al. | |
| 8,992,620 B2 | 3/2015 | Ashley et al. | |
| 9,028,550 B2 | 5/2015 | Shulock et al. | |
| 9,358,125 B2 | 6/2016 | JImenez et al. | |
| 9,532,883 B2 | 1/2017 | McLuen et al. | |
| 9,622,878 B2 | 4/2017 | Grotz | |
| 2002/0045945 A1 | 4/2002 | Liu | |
| 2002/0068976 A1 | 6/2002 | Jackson | |
| 2002/0068977 A1 | 6/2002 | Jackson | |
| 2003/0176926 A1 | 9/2003 | Boehm et al. | |
| 2004/0030387 A1 | 2/2004 | Landry et al. | |
| 2004/0049271 A1 | 3/2004 | Biedermann | |
| 2004/0054412 A1 | 3/2004 | Gerbec et al. | |
| 2004/0087947 A1 | 5/2004 | Lim et al. | |
| 2004/0153065 A1 | 8/2004 | Lim | |
| 2005/0021041 A1 | 1/2005 | Michelson | |
| 2005/0021145 A1 | 1/2005 | de Villiers et al. | |
| 2005/0033432 A1 | 2/2005 | Gordon | |
| 2005/0080422 A1 | 4/2005 | Otte et al. | |
| 2005/0113916 A1 | 5/2005 | Branch | |
| 2005/0149188 A1 | 7/2005 | Cook | |
| 2005/0171541 A1 | 8/2005 | Boehm | |
| 2005/0251258 A1 | 11/2005 | Jackson | |
| 2005/0273171 A1 | 12/2005 | Gordon | |
| 2005/0273174 A1 | 12/2005 | Gordon | |
| 2005/0278026 A1 | 12/2005 | Gordon | |
| 2005/0283244 A1 | 12/2005 | Gordon | |
| 2005/0283245 A1 | 12/2005 | Gordon | |
| 2006/0004453 A1 | 1/2006 | Bartish, Jr. et al. | |
| 2006/0015184 A1 | 1/2006 | Winterbottom et al. | |
| 2006/0058878 A1 | 3/2006 | Michelson | |
| 2006/0084986 A1 | 4/2006 | Grinberg et al. | |
| 2006/0122701 A1 | 6/2006 | Kister | |
| 2006/0129244 A1 | 6/2006 | Ensign | |
| 2006/0142859 A1 | 6/2006 | Mcluen | |
| 2006/0149385 A1 | 7/2006 | Mckay | |
| 2006/0195192 A1 | 8/2006 | Gordon et al. | |
| 2006/0229729 A1 | 10/2006 | Gordon | |
| 2006/0241770 A1 | 10/2006 | Rhoda et al. | |
| 2006/0253201 A1 | 11/2006 | Mcluen | |
| 2007/0043442 A1 | 2/2007 | Abernathie | |
| 2007/0050030 A1 | 3/2007 | Kim | |
| 2007/0050032 A1 | 3/2007 | Gittings et al. | |
| 2007/0055377 A1 | 3/2007 | Hanson et al. | |
| 2007/0191951 A1 | 8/2007 | Branch | |
| 2007/0255415 A1 | 11/2007 | Edie et al. | |
| 2007/0270963 A1 | 11/2007 | Melkent et al. | |
| 2007/0270968 A1 | 11/2007 | Baynham | |
| 2008/0021559 A1 | 1/2008 | Thramann | |
| 2008/0065222 A1 | 3/2008 | Hamada | |
| 2008/0114467 A1 | 5/2008 | Capote et al. | |
| 2008/0140207 A1 | 6/2008 | Olmos et al. | |
| 2008/0147194 A1 | 6/2008 | Grotz et al. | |
| 2008/0161933 A1 | 7/2008 | Grotz et al. | |
| 2008/0167657 A1 | 7/2008 | Greenhalgh | |
| 2008/0183204 A1 | 7/2008 | Greenhalgh et al. | |
| 2008/0221694 A1 | 9/2008 | Warnick et al. | |
| 2008/0275455 A1 | 11/2008 | Berry et al. | |
| 2008/0281346 A1 | 11/2008 | Greenhalgh et al. | |
| 2008/0288073 A1 | 11/2008 | Renganath et al. | |
| 2008/0300598 A1 | 12/2008 | Barreiro et al. | |
| 2008/0306488 A1 | 12/2008 | Altarac et al. | |
| 2008/0319487 A1 | 12/2008 | Fielding et al. | |
| 2008/0319549 A1 | 12/2008 | Greenhalgh et al. | |
| 2009/0024217 A1 | 1/2009 | Levy et al. | |
| 2009/0062833 A1 | 3/2009 | Song | |
| 2009/0076616 A1 | 3/2009 | Duggal et al. | |
| 2009/0125062 A1 | 5/2009 | Arnin | |
| 2009/0149956 A1 | 6/2009 | Greenhalgh et al. | |
| 2009/0149959 A1 | 6/2009 | Conner et al. | |
| 2009/0204218 A1 | 8/2009 | Richelsoph | |
| 2009/0222100 A1 | 9/2009 | Cipoletti et al. | |
| 2009/0240334 A1 | 9/2009 | Richelsoph | |
| 2009/0270989 A1 | 10/2009 | Conner et al. | |
| 2009/0281628 A1 | 11/2009 | Oglaza et al. | |
| 2009/0292361 A1 | 11/2009 | Lopez | |
| 2009/0299478 A1 | 12/2009 | Carls et al. | |
| 2009/0312763 A1 | 12/2009 | McCormack | |

(56)  References Cited

U.S. PATENT DOCUMENTS

| | | | |
|---|---|---|---|
| 2010/0049324 A1 | 2/2010 | Valdevit | |
| 2010/0070041 A1 | 3/2010 | Peterman | |
| 2010/0082109 A1 | 4/2010 | Greenhalgh et al. | |
| 2010/0145455 A1 | 6/2010 | Simpson et al. | |
| 2010/0179657 A1 | 7/2010 | Greenhalgh et al. | |
| 2010/0211176 A1 | 8/2010 | Greenhalgh | |
| 2010/0222816 A1 | 9/2010 | Gabelberger et al. | |
| 2010/0286783 A1 | 11/2010 | Lechmann et al. | |
| 2011/0035011 A1 | 2/2011 | Cain | |
| 2011/0093074 A1 | 4/2011 | Glerum et al. | |
| 2011/0160861 A1 | 6/2011 | Jimenez et al. | |
| 2011/0172774 A1 | 7/2011 | Varela | |
| 2011/0276142 A1 | 11/2011 | Niemiec et al. | |
| 2011/0301713 A1 | 12/2011 | Theofilos | |
| 2011/0319997 A1 | 12/2011 | Glerum et al. | |
| 2012/0035729 A1 | 2/2012 | Glerum et al. | |
| 2012/0059470 A1 | 3/2012 | Weiman | |
| 2012/0059472 A1 | 3/2012 | Weiman | |
| 2012/0059475 A1* | 3/2012 | Weiman | A61F 2/44 623/17.16 |
| 2012/0109308 A1 | 5/2012 | Lechmann et al. | |
| 2012/0130496 A1 | 5/2012 | Duffield et al. | |
| 2012/0165945 A1 | 6/2012 | Hansell et al. | |
| 2012/0185049 A1 | 7/2012 | Varela | |
| 2012/0209386 A1 | 8/2012 | Triplett et al. | |
| 2012/0215313 A1 | 8/2012 | Saidha et al. | |
| 2012/0226357 A1 | 9/2012 | Varela | |
| 2012/0265309 A1 | 10/2012 | Glerum et al. | |
| 2012/0277861 A1 | 11/2012 | Steele et al. | |
| 2012/0277870 A1 | 11/2012 | Wolters et al. | |
| 2012/0323329 A1 | 12/2012 | Jimenez et al. | |
| 2012/0330426 A1 | 12/2012 | McLaughlin et al. | |
| 2013/0023993 A1 | 1/2013 | Weiman | |
| 2013/0023994 A1 | 1/2013 | Glerum | |
| 2013/0158663 A1 | 6/2013 | Miller et al. | |
| 2013/0158669 A1 | 6/2013 | Sungarian et al. | |
| 2013/0197647 A1 | 8/2013 | Wolters et al. | |
| 2013/0211526 A1 | 8/2013 | Alheidt et al. | |
| 2013/0274883 A1 | 10/2013 | McLuen et al. | |
| 2014/0067071 A1 | 3/2014 | Weiman et al. | |
| 2014/0088714 A1 | 3/2014 | Miller et al. | |
| 2014/0163683 A1 | 6/2014 | Seifert et al. | |
| 2014/0277473 A1* | 9/2014 | Perrow | A61F 2/4455 623/17.15 |
| 2015/0066145 A1 | 3/2015 | Rogers et al. | |
| 2015/0088258 A1 | 3/2015 | Jimenez et al. | |
| 2015/0134064 A1 | 5/2015 | Grotz et al. | |
| 2015/0216676 A1 | 8/2015 | Shulock et al. | |
| 2015/0289988 A1 | 10/2015 | Ashley et al. | |
| 2015/0374508 A1 | 12/2015 | Sandul | |
| 2016/0166396 A1 | 6/2016 | McClintock | |
| 2016/0324654 A1 | 11/2016 | Loebl et al. | |
| 2017/0100258 A1 | 4/2017 | Jimenez et al. | |
| 2017/0119543 A1 | 5/2017 | Dietzel et al. | |

FOREIGN PATENT DOCUMENTS

| | | | |
|---|---|---|---|
| DE | 4327054 C1 | 4/1995 | |
| EP | 0576379 B1 | 6/1993 | |
| EP | 0610837 B1 | 7/1994 | |
| EP | 3111896 A1 | 1/2017 | |
| FR | 2794968 A1 | 12/2000 | |
| JP | 2000-513263 A | 10/2000 | |
| KR | 200290058 Y1 | 9/2002 | |
| SU | 1424826 A1 | 9/1988 | |
| WO | 9201428 A1 | 2/1992 | |
| WO | 9525485 A1 | 9/1995 | |
| WO | 1999042062 A1 | 8/1999 | |
| WO | 1999066867 A1 | 12/1999 | |
| WO | 2002045625 A1 | 6/2002 | |
| WO | 2004019829 A1 | 3/2004 | |
| WO | 2004069033 A2 | 8/2004 | |
| WO | 2006045094 A2 | 4/2006 | |
| WO | 2006047587 A2 | 5/2006 | |
| WO | 2006113080 A2 | 10/2006 | |
| WO | 2008044057 A1 | 4/2008 | |
| WO | 2008134515 A1 | 11/2008 | |
| WO | 2009114381 A1 | 9/2009 | |
| WO | 2010103344 A1 | 9/2010 | |
| WO | 2012031267 A1 | 3/2012 | |
| WO | 2015009793 A1 | 1/2015 | |

* cited by examiner

EXPANDING INTERVERTEBRAL IMPLANTS

CROSS REFERENCE TO RELATED APPLICATIONS

This application is a continuation of U.S. patent application Ser. No. 17/699,752 filed on Mar. 21, 2022, which is a continuation of U.S. patent application Ser. No. 16/902,921 filed on Jun. 16, 2020, all of which are incorporated in their entirety herein.

FIELD OF THE INVENTION

This invention relates to stabilizing adjacent vertebrae of the spine by inserting an intervertebral spacer, and more particularly an intervertebral spacer that is adjustable in height.

BACKGROUND OF THE INVENTION

The vertebral or spinal column (spine, backbone) is a flexible assembly of vertebrae stacked on top of each other extending from the skull to the pelvic bone which acts to support the axial skeleton and to protect the spinal cord and nerves. The vertebrae are anatomically organized into four generalized body regions identified as cervical, thoracic, lumbar, and sacral; the cervical region including the top of the spine beginning in the skull, the thoracic region spanning the torso, the lumbar region spanning the lower back, and the sacral region including the base of the spine ending with connection to the pelvic bone. With the exception of the first two cervical vertebrae, cushion-like discs separate adjacent vertebrae, i.e. intervertebral discs.

The stability of the vertebral column during compression and movement is maintained by the intervertebral discs. Each disc includes a gel-like center surrounded by a fibrous ring. The gel-like center, i.e. nucleus pulposus, provides strength such that the disc can absorb and distribute external loads and contains a mixture of type II-collagen dispersed in a proteoglycan matrix. The fibrous ring, or annulus fibrosus, provides stability during motion and contains laminated rings of type-I collagen. Thus, the annulus fibrosis and the nucleus pulposus are interdependent, as the annulus fibrosis contains the nucleus pulposus in place and the nucleus pulposus aligns the annulus fibrosus to accept and distribute external loads. The integrity of the composition and structure of the intervertebral disc is necessary to maintain normal functioning of the intervertebral disc.

Many factors can adversely alter the composition and structure of the intervertebral disc, such as normal physiological aging, mechanical injury/trauma, and/or disease, resulting in impairment or loss of disc function. For example, the content of proteoglycan in the nucleus pulposus declines with age, thus, it follows that the ability of the nucleus pulposus to absorb water concurrently declines. Therefore, in normal aging the disc progressively dehydrates, resulting in a decrease in disc height and possible de-lamination of the annulus fibrosus. Mechanical injury can tear the annulus fibrosis allowing the gel-like material of the nucleus pulposus to extrude into the spinal canal and compress neural elements. Growth of a spinal tumor can impinge upon the vertebrae and/or disc potentially compressing nerves.

Bones of the spine, and bony structures, generally, are susceptible to a variety of weaknesses that can affect their ability to provide support and structure. Weaknesses in bony structures have numerous potential causes, including degenerative diseases, tumors, fractures, and dislocations. Advances in medicine and engineering have provided doctors with a plurality of devices and techniques for alleviating or curing these weaknesses.

In some cases, the spinal column, in particular, requires additional support in order to address such weaknesses. One technique for providing support is to insert a spacer between adjacent vertebrae.

SUMMARY OF THE INVENTION

A device of the disclosure for separating bones of a joint using a driver tool having a threaded shaft, comprises a superior endplate having a bone engaging surface and a surface opposite the bone engaging surface having ramps including at least two inferior facing ramps; an inferior endplate having a bone engaging surface and a surface opposite the bone engaging surface having ramps including at least two superior facing ramps; first and second bearings disposed between the first and second endplates, each having ramps including at least one superior facing ramp mateably engaged with an inferior facing ramp of the superior endplate, and at least one inferior facing ramp mateably engaged with a superior facing ramp of the inferior endplate, the first bearing including a threaded aperture, the second bearing including a thrust surface; the threaded aperture threadably engageable with the threaded shaft of the driver tool, the thrust surface aligned with the threaded shaft to be pushable by the threaded shaft when the threaded shaft is threaded through the threaded aperture to thereby cause the first and second bearings to be driven apart, whereby the ramps of the first and second bearings bear against the ramps of the superior endplate and the ramps of the inferior endplate to thereby push the superior endplate away from the inferior endplate.

In variations thereof, the threaded aperture disposed at a non-orthogonal angle with respect to a longitudinal axis of the device; at least one of the bone engaging surface of the superior endplate and the bone engaging surface of the inferior endplate having an opening through which bone can grow; the ramps of the first and second bearings and the at least two ramps of the superior endplate and the at least two ramps of the inferior endplate are oriented at a non-orthogonal angle with respect to a longitudinal axis of the device; and/or the first and second bearings are displaced relative to each other along the longitudinal axis of the device when the first and second bearings are pushed apart by the driver.

In further variations thereof, the device further includes the threaded driver; the driver includes a threaded end and a handle, the threaded end separable from the handle, whereby the threaded end can remain with the device within the body; a leading end of at least one of the superior endplate and the inferior endplate provided with an angular profile, whereby a leading end of the device has a tapering leading end profile; the threaded aperture forming an acute angle with respect to a longitudinal axis of the device which opens in a direction away from the leading end; and/or the device includes no more than 5 parts, limited to the superior and inferior endplates, the first and second bearings, and the threaded shaft.

In yet further variations thereof, the device further includes a radiopaque material; the superior and inferior endplates, and the first and second bearings all mutually nest when the device is in a collapsed configuration to thereby present a reduced radial profile to facilitate insertion of the device into a patient; and/or ramps of the bearings being at least one of recessed relative to a surrounding surface and projecting relative to a surrounding surface, wherein when a mating ramp of the superior endplate and a mating ramp of the inferior endplate are mated to a recessed bearing ramp, the mating ramp is projecting relative to a surrounding surface, and when a mating ramp of the superior endplate and a mating ramp of the inferior endplate are mated to a projecting bearing ramp, the mating ramp is recessed relative to a surrounding surface.

In a method of the disclosure, separating bones of a joint comprises inserting a spacer through an opening in Kambin's triangle, the spacer having: a superior endplate having a bone engaging surface and a surface opposite the bone engaging surface having ramps including at least two inferior facing ramps; an inferior endplate having a bone engaging surface and a surface opposite the bone engaging surface having ramps including at least two superior facing ramps; first and second bearings disposed between the first and second endplates, each having ramps including at least one superior facing ramp mateably engaged with an inferior facing ramp of the superior endplate, and at least one inferior facing ramp mateably engaged with a superior facing ramp of the inferior endplate, the first bearing including a threaded aperture, the second bearing including a thrust surface; the threaded aperture threadably engageable with the threaded shaft of the driver tool, the thrust surface aligned with the threaded shaft to be pushable by the threaded shaft when the threaded shaft is threaded through the threaded aperture to thereby cause the first and second bearings to be driven apart, whereby the ramps of the first and second bearings bear against the ramps of the superior endplate and the ramps of the inferior endplate to thereby push the superior endplate away from the inferior endplate; rotating the driver tool to cause pushing of the inferior endplate away from the superior endplate to restore a therapeutic alignment of the bones of the joint; removing the driver tool to leave the threaded shaft within the device.

In variations thereof, the spacer has a tapered leading end, the threaded aperture disposed at an acute angle opening in a direction away from the tapered leading end, the method further including pushing the device into the body using a tool engaged with the threaded aperture; the ramps of the first and second bearings and the at least two ramps of the superior endplate and the at least two ramps of the inferior endplate are oriented at a non-orthogonal angle with respect to a longitudinal axis of the device, the method further including rotating the driver tool to cause displacement of the first and second bearings relative to each other along the longitudinal axis of the device; and/or the driver tool having a handle coupled to the threaded shaft, the method further including uncoupling the handle from the threaded shaft.

In other variations thereof, the method further includes selecting an endplate from among a plurality of endplates each having a relatively different lordotic profiles; the spacer including opening to an interior of the spacer, the method further including inserting a bone growth material into the opening; and/or the bone growth material selected from at least one of an autograft, allograft, xenograft, and bone substitute.

BRIEF DESCRIPTION OF THE DRAWINGS

A more complete understanding of the disclosure, and the attendant advantages and features thereof, will be more readily understood by reference to the following detailed description when considered in conjunction with the accompanying drawings, in which.

DETAILED DESCRIPTION OF THE INVENTION

Figures 1, 2, 3:
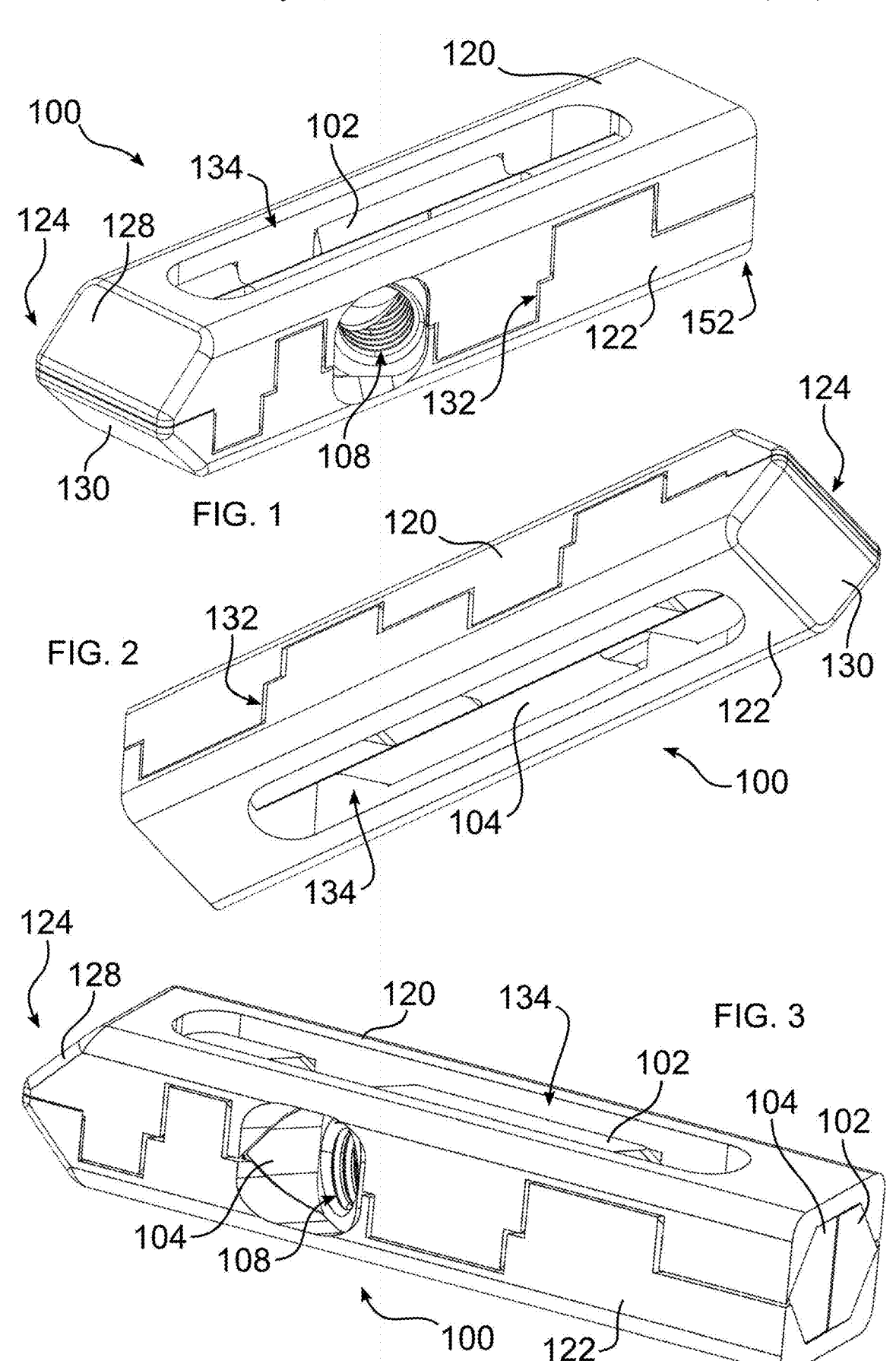
FIG. 1 is a front perspective view of a spacer device of the disclosure.
FIG. 2 is a lower perspective view of the device of FIG. 1.
FIG. 3 is a rear perspective view of the device of FIG. 1.

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language).

With reference to the figures, the disclosure provides an expandable spacer/implant or device 100 having an adjustable height. Device 100 is inserted between two adjacent bony surfaces to facilitate separation of the bones, and if desired, to promote the fusion of bony surfaces. Although intended to be useful with any adjacent bony surface in which fusion is desired, device 100 is advantageously applied to insertion between two adjacent vertebral bodies in any section of the spine, including the cervical, thoracic, lumbar, and sacral vertebral sections. More than one device 100 may be implanted within the body, for example between successive or separated vertebrae, or positioned between the same adjacent vertebrae. The use of multiple devices 100 is particularly advantageous for patients whose back pain is not limited to a localized area, or for patients whose localized damage has progressed to other areas of the spine.

Device 100 and methods for its insertion can be used in a treatment protocol for any of a wide variety of conditions in a patient involving diseased or damaged bony structures. The patient can be a human being. Additionally, it is contemplated that device 100 may be useful in veterinary science for any animal having adjacent bony structures to be fused. Devices 100 can expand to roughly twice its fully reduced insertion height. When in this collapsed configuration, device 100 can be inserted into a space through a small incision and narrow pathways, using appropriate minimally-invasive techniques, and can be positioned within the space between adjacent bones, and there expanded to a desired therapeutic height. The incision may be short, for example about one centimeter in length, which is smaller than device 100 in an expanded configuration. If the desired position and/or expansion are not achieved, device 100 can be collapsed, repositioned, and re-expanded in situ.

Although device 100 is exemplified herein for use in the spine, device 100 is contemplated for fusion of any bony structures. While devices 100 are described herein using several varying embodiments, devices 100 are not limited to these embodiments. An element of one embodiment may be used in another embodiment, or an embodiment may not include all described elements.

Interbody devices have been used to provide support and stability in the anterior column of the spinal vertebrae when treating a variety of spinal conditions, including degenerative disc disease and spinal stenosis with spondylolisthesis. Clinical treatment of spinal pathologies with anterior vertebral body interbody devices relies on precise placement of interbodies to restore normal anterior column alignment. Iatrogenic pathologies may result from both the surgical access window to the disc space, failure to precisely place the interbody on hard cortical bone often found on the apophyseal ring of the vertebral body, or failure to precisely control and restore normal anatomical spinal alignment. Device 100 provides for the precise placement of interbody support that both increases interbody contact with hard cortical bone and provides precise control of anterior column alignment while reducing the profile of the access window to the disc space.

More particularly, in order to improve the access profile of the interbody while maximizing cortical bone contact surface area, device 100 enters the disc space with a narrow profile and can be positioned upon the anterior apophyseal ring. The orientation and position of the interbody in its final implanted position may be optimized by pre-/intra-op scans or normal population statistics that determine bone mineral density maps of the vertebral body. Robotic and navigation guidance may be used to correctly orient the interbody.

In an embodiment, device 100 can be implanted as follows:

1. A determination is made on final optimal implant location to optimize bone mineral density of the contacted bone/implant interface.
2. Robotic/navigation is used to determine the potential trajectories that will allow for this optimal implant location to be achieved.
3. A cannula is docked on the disc space through Kambin's triangle, or the anatomical area that is bordered by the disc space, exiting nerve root, and traversing nerve root.
4. The expandable interbody is inserted in the non-expanded orientation (FIGS. 1-3) into contact with, for example, the anterior apophyseal ring of the vertebral body (FIGS. 7-8, 21, and 27).
5. The expandable interbody is expanded to precisely achieve a therapeutic spinal alignment.

With reference to the drawings, device 100 is expanded using a slide system which causes the separation of endplates 120 and 122, which are each positioned within the body to contact a separate side of a bone joint relative to the other endplate. When positioned within the spine, one endplate will be a superior endplate contacting a more superior vertebra, and the other endplate will be an inferior endplate, contacting a more inferior vertebra. An orientation of device 100 may be determined by the side of the body from which implantation is approached. For convenience, herein, endplate 120 will be designated as superior, although it should be understood that endplate 122 could be designated as superior.

Figures 4, 5, 6:
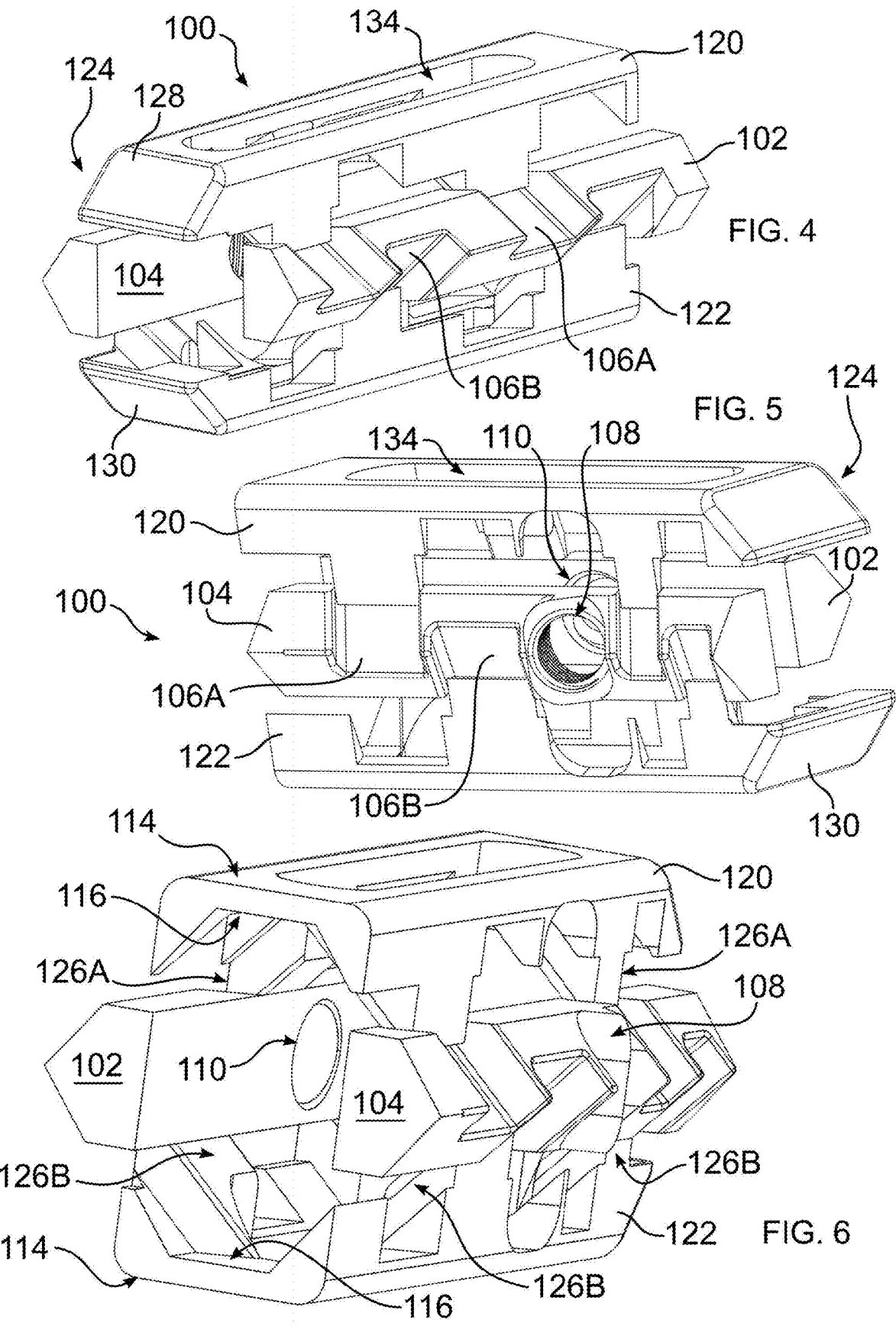
FIG. 4 is a front perspective view of an opposite side of the device of FIG. 1, in an expanded configuration.
FIG. 5 is a front perspective view of the device of FIG. 1, radially rotated, and in an expanded configuration.
FIG. 6 is a rear perspective view of the device of FIG. 1, in an expanded configuration.
Figures 7, 8, 9:
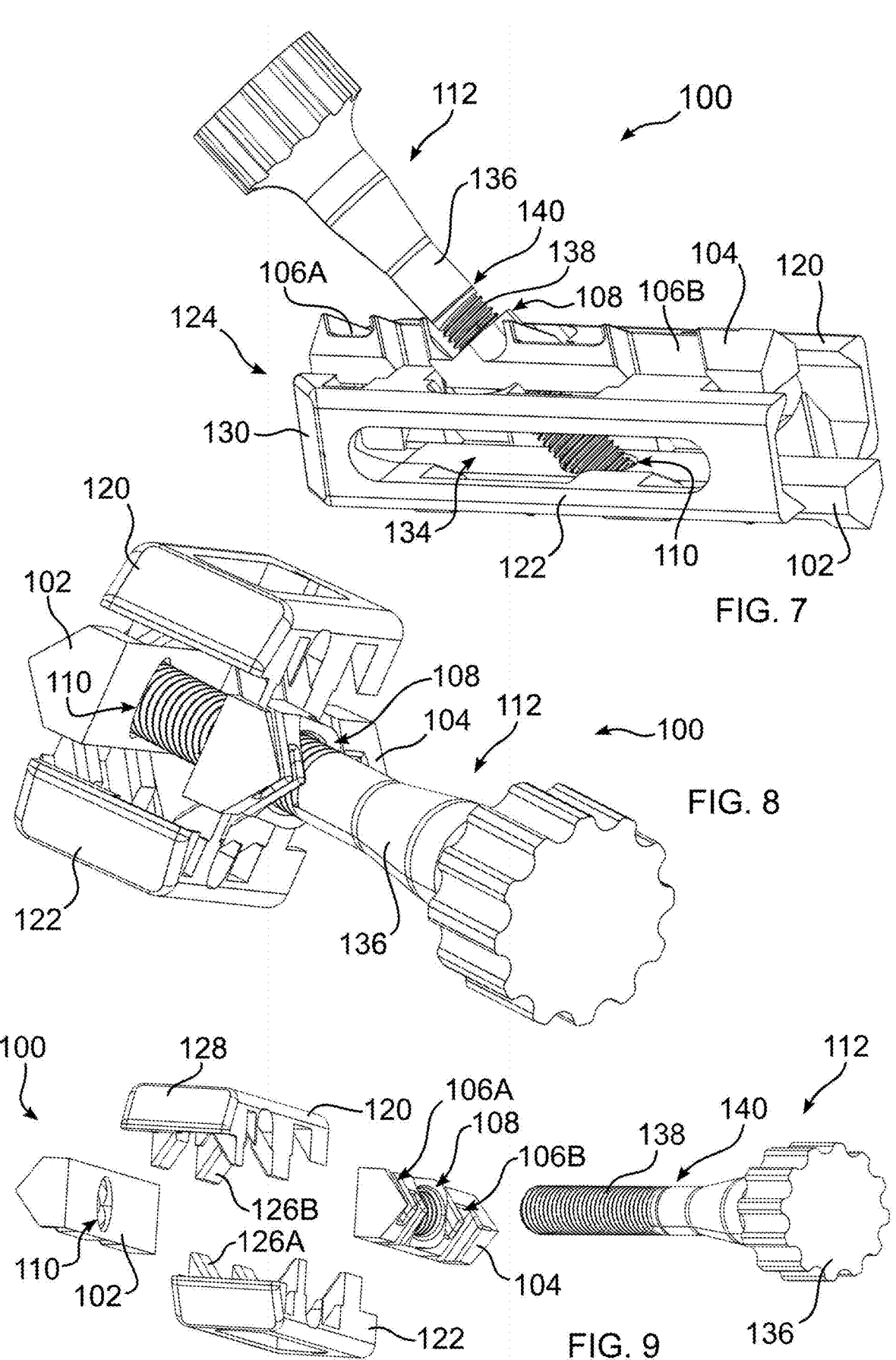
FIG. 7 is a perspective view of the device of FIG. 1, in an expanded configuration, including a driver tool threaded into the device.
FIG. 8 is an alternative perspective of the device of FIG. 7.
FIG. 9 is an exploded perspective view of the device of FIG. 7.

In particular, and with reference to FIGS. 4-6, device 100 includes first and second internal bearings 102, 104 each having one or more superior facing ramps 106A, and one or more inferior facing ramps 106B (collectively ramps 106). In the figures, ramps 106 are illustrated as being recessed relative to surrounding surfaces, however one or all of ramps 106 can alternatively project from surrounding surfaces. Ramps 106A extend transverse to the central longitudinal axis of device 100 and are angled from an inferior position distal to the central longitudinal axis to a superior position proximal to the central longitudinal axis. Ramps 106B likewise extend transverse to the central longitudinal axis of device 100 but are angled from a superior position distal to the central longitudinal axis to an inferior position proximal to the central longitudinal axis.

Bearing 104 includes a threaded through-bore 108 disposed at an angle relative to the central longitudinal axis of device 100. Bearing 102 includes a thrust surface 110, in the embodiment shown having the form of a blind-hole or capture bore that is axially aligned with through-bore 108. A driver 112 including a handle 136 and a separable set screw 138 can be threaded into through-bore 108 to then pass into thrust surface 110 and can rotate within thrust surface 110 as driver 112 is rotated to thereby cause bearings 102 and 104 to be forced apart to expand device 100, as described further below. After expansion, handle 136 can be separated from set screw 138 at coupling 140. As bearing 104 is contacted by driver 112, it would typically be considered the proximal bearing, and bearing 102 the distal bearing.

By forming thrust surface as a bore, driver 112 is captured by both bearings 102, 104, to thereby maintain a predetermined orientation and alignment of bearings 102, 104 as they move relative to each other. Thrust surface 110 can alternatively have the form of a flat surface, and another form of guide for bearings 102, 104 can be provided, such as one or more rails (not shown) extending between or through bearings 102, 104.

Endplates 120, 122 each include a bone facing outer side 114 and a mutually facing inner side 116. Each inner side 116 of endplate 120 includes one or more inferior facing ramps 126B, and each inner side 116 of endplate 122 includes one or more superior facing ramps 126A. In the figures, ramps 126 are illustrated as projecting relative to surrounding surfaces, however one or all of ramps 126 can alternatively be recessed from surrounding surfaces. However, where ramps 106 project, ramps 126 advantageously are recessed, whereby this inverse relationship helps to maintain an axial alignment between ramps 106 and 126 when mutually engaged. Ramps 126A extend transverse to the central longitudinal axis of device 100 and are angled from an inferior position distal to the central longitudinal axis to a superior position proximal to the central longitudinal axis. Ramps 126B likewise extend transverse to the central longitudinal axis of device 100 but are angled from a superior position distal to the central longitudinal axis to an inferior position proximal to the central longitudinal axis.

Endplates 120, 122 and bearings 102, 104 are collectively engaged to form an assembled device 100 by mating endplate ramps 126A with bearing ramps 106A, and mating endplate ramps 126B with bearing ramps 106B. In a collapsed configuration of device 100, ramps 106A and ramps 126A are engaged over a greater mutual surface than when device 100 is in an expanded configuration. To cause expansion, driver 112 is threaded into through-bore 108 to bear against thrust surface 110, and to thereby cause separation of bearings 102, 104 as driver 112 is further rotated. As bearings 102, 104 separate, ramps 126A are driven superiorly against ramps 106A, and ramps 126B are driven inferiorly against ramps 106B. As a result, endplates 120 and 122 are mutually separated, increasing a height of device 100.

Ramps 106 can be of equal shape and size, and ramps 126 can be of equal shape and size, and bone facing outer side 114 of bearings 120 and 122 can be parallel when collapsed, whereby the bone facing sides 114 of endplates 120 and 122 will remain parallel as device 100 is expanded. Alternatively, ramps 106 and 126 can have alternative shapes which cause unequal expansion which can be used to adjust for lordosis. The unequal expansion can be caused, by the ramp 106, 126 shapes and sizes, to occur along the long axis of device 100, or along an axis transverse to the long axis of device 100. Alternatively, bone facing sides 114 of endplates 120, 122 can be non-parallel when collapsed, and this non-parallel relationship can be maintained during expansion by equal ramp 106, 126 shapes and sizes, or the non-parallel relationship can be changed during expansion by unequal ramp 106, 126 shapes and sizes.

As can best be seen in FIGS. 1-3, ramps 106 and 126 are sized and dimensioned to nest, for example along line 132, as completely as possible, so that a collapsed profile of device 100 is as small as possible. When collapsed, device 100 is provided with a tapered leading end 124 which facilitates insertion of device 100 into the body. Tapering leading end 124 is formed from a leading portion 128 of endplate 120 and a leading portion 130 of endplate 122, which are mutually adjacent when device 100 is collapsed, as would be the case during implantation.

Advantages of the disclosure include, at least:
1. A small insertion profile: The disclosure enables, for example, an 8.5 mm insertion profile into the disc space, reducing the required skin, fascia, muscle, and ligamentous disruption. Smaller profiles can be achieved, including profiles as small as 6 mm, for example, or profiles substantially larger than 8.5 mm, in each case limited only by the needs dictated by a particular patient's anatomy.
2. Controlled lordosis: The disclosure enables controlled lordosis through placement of device 100 in a collapsed position on the anterior apophyseal ring within the disc space. With the spacer placed horizontally across the disc space, and due to the fact that the spacer has a relatively small depth, the spacer can be used in one application as a fulcrum to increase lordosis as it is expanded, if therapeutically beneficial. It is generally accepted that placing the spacer on the anterior apophyseal ring provides the most leverage for continuously increasing lordosis as it is expanded in height. However, more posterior placement can also be utilized as this can allow for increased anterior height when leveraging using the same height spacer. Alternatively, two devices 100 can be placed between the same vertebrae, one in the anterior aspect of the vertebral body and one in the posterior aspect of the vertebral body, to further control and adjust sagittal balance by then allowing independent expansion of the anterior and posterior aspects of the vertebral body.
3. Reduced endplate disruption: Due to the ability of device 100 to expand a correct, therapeutic extent in situ, the disclosure reduces the need for traditional trialing through the insertion of interbody implants of various sizes, the latter potentially causing or contributing to vertebral endplate disruption and further trauma to the body.

With reference to FIGS. 18-21, an implantation tool 400 forms a cannula. Indicia 402 indicate an insertion depth of tool 400 into the body. Positioning is carried out using imaging, and can further be carried out using a robotics system. The bore 404 of tool 400 enables the insertion of surgical instruments in order to cut, excise, or cauterize body tissue, and to otherwise facilitate a surgical procedure to implant device 100. Bore 404 is further sized to enable passage of device 100. To minimize the required size of bore 404, device 100 is configured in the collapsed configuration, which is the smallest height profile, with driver 112 disengaged.

After device 100 exits tool 400 within the body, it may be manipulated into a position upon the vertebral endplate 300, for example upon the apophyseal ring 302, using surgical tools passed through tool 400. After device 100 is positioned, driver 112 is passed through tool 400 and engaged with through-bore 108. Alternatively, tool 400 is removed prior to insertion of driver 112. Tool 400 can be removed after engagement between driver 112 and through-bore 108, as determined by the practitioner and the applicable protocol.

Figures 22, 23, 24, 25, 26, 27:
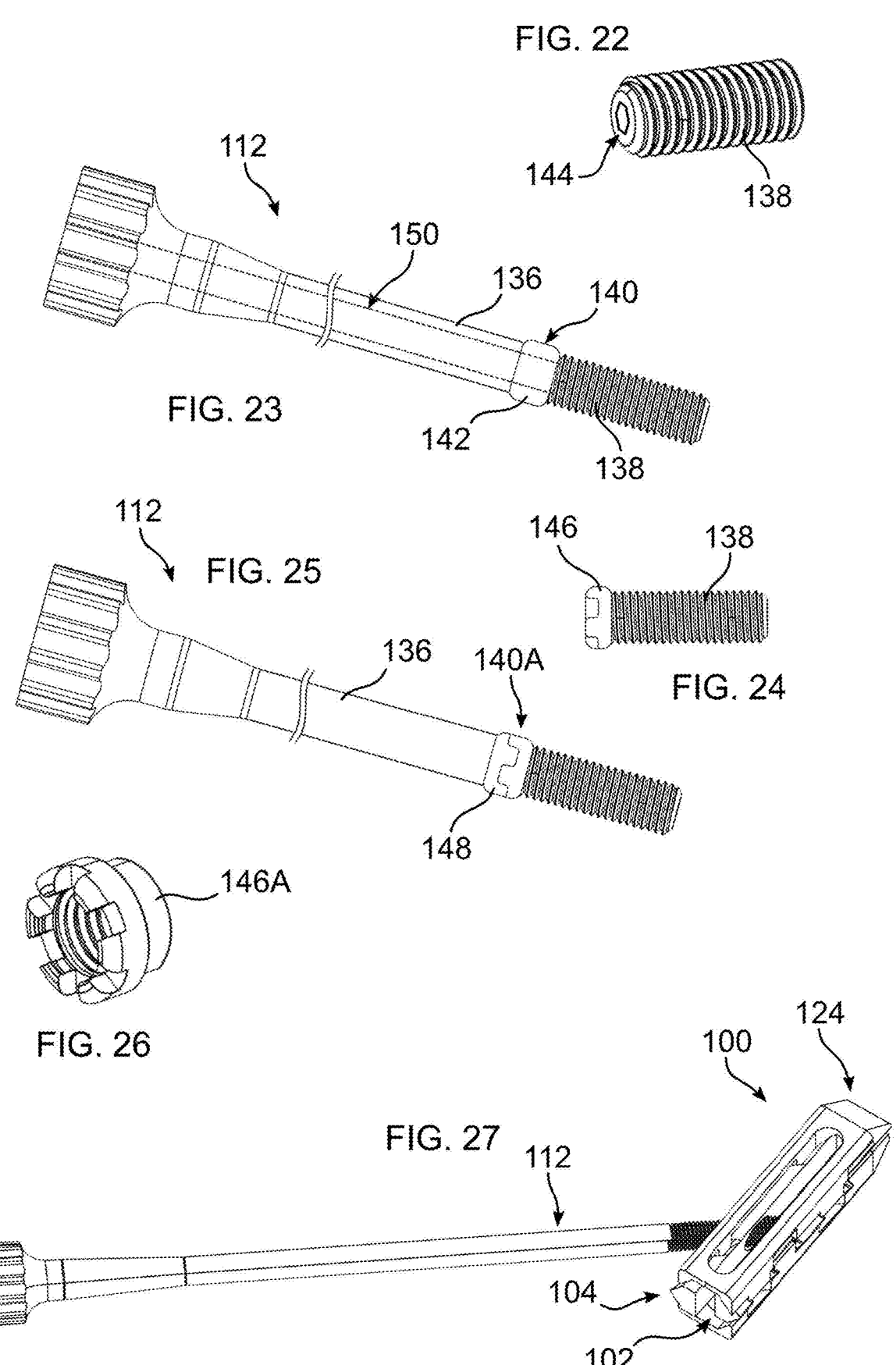
FIGS. 22 and 23 illustrate a handle with a coupling portion.
FIGS. 24 and 25 illustrate the coupling portion.
FIG. 26 illustrates a castle nut portion according one embodiment of the invention.
FIG. 27 illustrates the device in an expanded configuration.

Engaged driver 112 can be rotated to cause expansion of device 100 as described above. At a later date, if needed, tool 400 can be reinserted into the body to reposition device 100, change a height of device 100 using driver 112, and/or device 100 can be removed from the body if therapeutically beneficial. With reference to FIGS. 22-26, a coupling 140 enables separation of driver handle portion 136 and set screw 138. In FIGS. 22-23, handle 136 includes a coupling portion 142 which includes an internal thread mateable with set screw 138, whereby after set screw 138 is fully engaged, further rotation of handle 136 causes rotation of set screw 138. Rotating handle 136 in an opposite direction disengages handle 136 from set screw 138. Set screw 138 includes a tool engagement 144 which can be used to reverse rotation of set screw 138, for example to collapse device 100, or to prevent rotation of set screw 138 as handle 136 is unthreaded from set screw 138. To engage set screw 138, a tool is inserted through a central bore 150 through handle 112 and coupling 140. A hex engagement is illustrated, although any other suitable type of engagement can be used.

Device can be passed into the body with tapering leading end 124 inserted first. The chamfered or tapering profile of leading end 124, which can be different than the profile illustrated, reduces disruption and potential trauma to the body by having smooth rounded edges, and by gradually separating tissue due to the tapered profile. Accordingly, device 100 is advantageously passed into the body in a leading end 124 first orientation.

In place of implantation tool 400, driver 112 can be threaded into through-bore 108, after which driver 112 can be used to manipulate device 100 into a desired position within the body. In the illustrations, through-bore 108 and thrust surface 110 are angularly disposed within bearings 102, 104 to enable driver 112 to be inserted through a, typically, separate pathway to device 100 within the body. As can be seen best in FIGS. 1 and 7, driver 112 must be threaded into through-bore 108 by approaching from a direction passing towards leading end 124. As such, the angular disposition of the through-bore forms an acute angle with the longest longitudinal axis of the device, which opens in a direction towards leading end 124.

However, with reference to FIG. 27, it may be seen that through-bore 108 and thrust surface 110 can be positioned anywhere along bearings 102, 104, and can be disposed at other angular orientations. As shown in FIG. 27, through-bore 108 and thrust surface 110 are now positioned further from leading end 124, and are angled in an opposite direction, with respect to depictions in other figures herein. As such, the angular disposition of the through-bore forms an acute angle with the longest longitudinal axis of the device, which opens in a direction away from leading end 124. This positions and angles driver 112, when threaded into through-bore 108, to approach through the same pathway into the body as device 100. Moreover, driver 112 can function as an implantation tool which can be used to manipulate device 110 into a therapeutic position within the body. After implantation in this manner, and without a requirement of removing driver 112 or changing tools, driver 112 can further function to be rotated to increase a height of device 100 to address skeletal stability. After adjusting a height of device 100, handle 136 is removed as described with respect to FIGS. 22-26, or in some other manner.

Figures 10, 11, 12, 13:
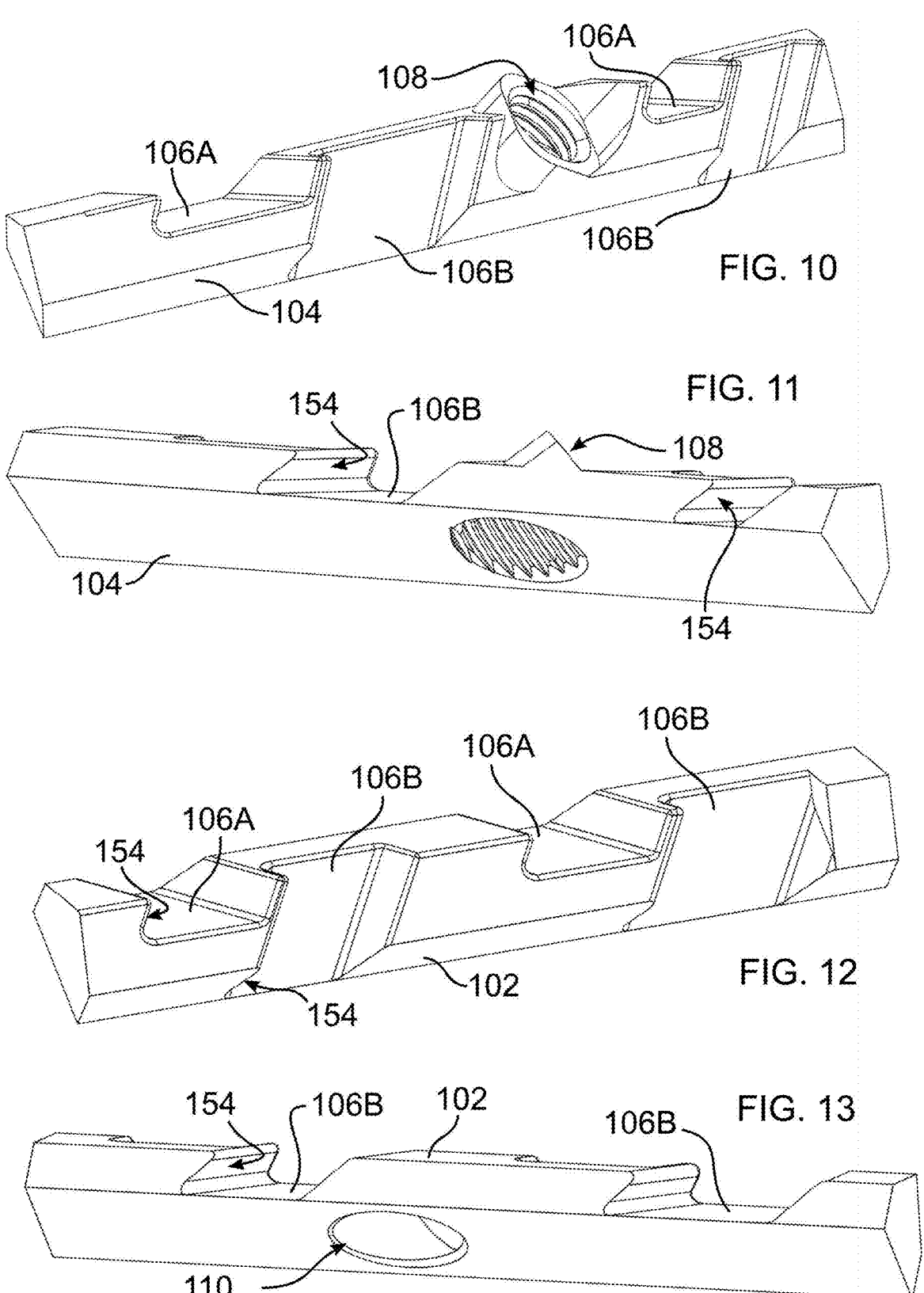
FIGS. 10-11 are perspective views of a bearing of the device of FIG. 1, which includes a threaded through-bore engageable with the driver tool.
FIGS. 12-13 are perspective views of another bearing of the device of FIG. 1, which includes a thrust surface aligned with the through-bore of the bearing of FIGS. 10-11.
Figures 14, 15, 16, 17:
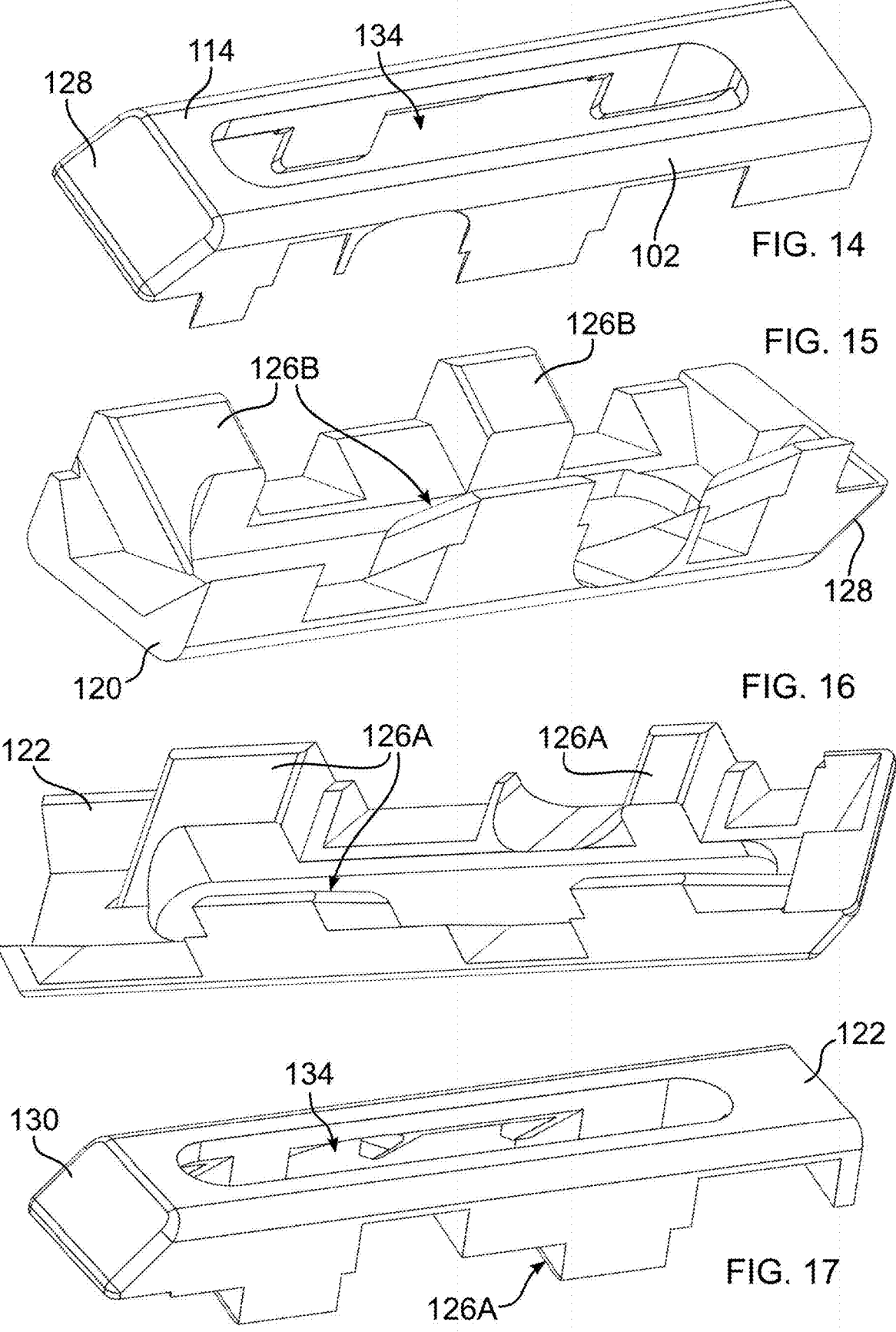
FIGS. 14-15 are perspective views of a superior endplate of the device of FIG. 1.
FIGS. 16-17 are perspective views of an inferior endplate of the device of FIG. 1.
Figures 18, 19, 20, 21:
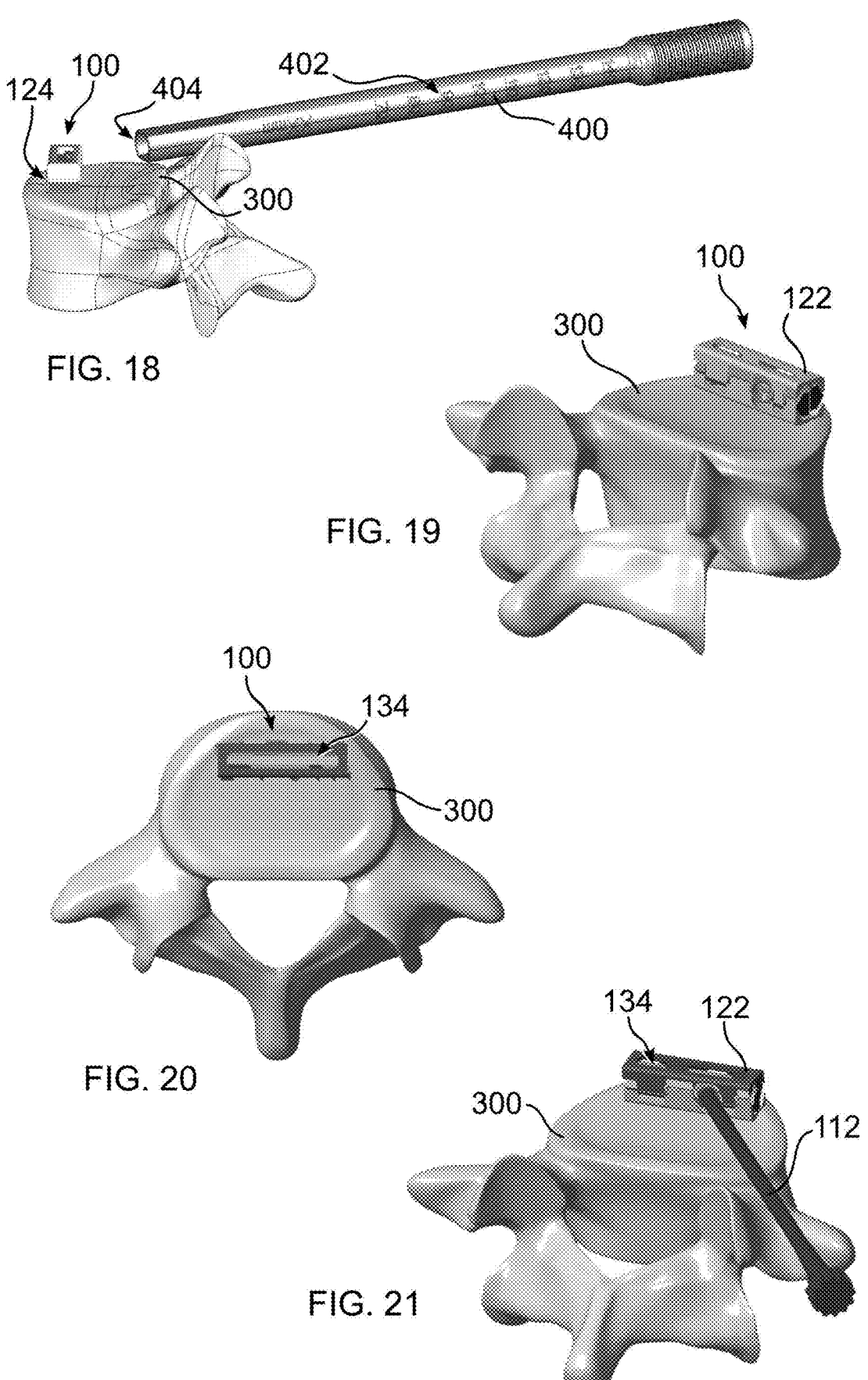
FIG. 18 is a diagrammatic view of the device of FIG. 1 in position upon a bone surface, the device having been inserted into the body using a cannula tool.
FIG. 19-20 are alternative perspective view of the device and bone of FIG. 18.
FIG. 21 is a perspective view of the device and bone of FIG. 18, with an expansion driver tool mounted within the device and extending outside of the body.

FIG. 27 further depicts device 100 in an expanded configuration, wherein it may be seen that bearings 102 and 104 have become relatively displaced along the longitudinal axis of device 100, as a result of being driven apart. Accordingly, ramps 106, 126 must be relatively sized and/or angularly disposed to enable this longitudinal displacement of bearings 102, 104. As can best be seen, for example, in FIG. 12, bearing ramps 106A, 106B are disposed at a non-orthogonal angle with respect to a longitudinal axis of device 100, the longitudinal axis being the longest axis of device 100, which extends from leading end 124 to trailing end 152 (FIG. 1). Ramps 126 of the superior and inferior endplates are angled to mate with the angle of ramps 106, to thereby enable relative movement of the bearings along the longitudinal axis when bearings 102, 104 are separated by being driven apart by driver 112.

As can additionally be seen in FIGS. 10-13, sidewalls 154 of ramps 106A, 106B can optionally be provided with dovetail surfaces which mate with dovetailed surfaces of ramps 126A, 126B (not shown in dovetail form). This can help to ensure that endplates 120, 122 remain in engagement with bearings 102, 104.

In FIGS. 24-25, coupling 140A includes a castle nut end portion 146 on set screw 138, and a mating castle nut end portion 148 on handle 136. FIG. 26 depicts a castle nut portion 146A which can be removed from set screw 138.

Different devices 100 may include ramps 106, 126 of differing height and length relative to other devices 100, to enable expansion at different rates or extents, as indicated for therapeutic treatment. Fewer or a greater number of ramps 106, 126 can be provided. Endplates 120, 122 may additionally, or alternatively, be resilient, so that they may conform to bony surfaces, forming a more stable support platform. Accordingly, endplates 120, 122 can be fabricated from a polymeric material, a naturally resilient material, or a resilient metal, for example a shape memory alloy, or any other resilient biocompatible material of sufficient strength and durability for separating bones within the body.

Device 100 can be inserted at a contracted height transforaminally, for example, and is capable of being positioned into anterior placement. Once placement is achieved, device 100 is capable of expanding for disc height restoration. Additionally, device 100 can be positioned anteriorly, and can be expanded through a continuous range to provide axial balance and greater endplate contact area. Additionally, device 100 enables superior sagittal correction, through the use of a relatively smaller insertion window, decreasing the need for bone damage. Thus, device 100 provides the benefits of an ALIF device through a familiar posterior approach, decreasing surgery time and associated blood loss, as well as eliminating the need for an access surgeon.

In accordance with the disclosure, during implantation of intervertebral spacers from a posterior approach, there is a need to avoid damaging nerve roots. A prior art spacer dimensioned to separate bones can block a view of nerve roots as it is inserted, and due to its large size, poses a greater risk of contacting nerve roots during insertion into the body. As a result, the medical practitioner must more often retract nerve roots, with attendant danger of tissue damage. Devices 100 of the disclosure form a smaller dimension during implantation, relative to a final dimension for spacing bones. Accordingly, nerve roots can be visualized and avoided during insertion, and nerve root manipulation can be avoided or minimized.

As devices 100 of the disclosure have a much smaller collapsed profile, they can be inserted between bones by being passed through a minimally invasive entry, for example through an incision approximating the smallest collapsed dimension, for example transverse to the longitudinal dimension. This enables exceptional anterior placement without impaction, as well as facilitating implantation from other approaches. Devices 100 of the disclosure further develop a good bone contact area, as an implant with a larger footprint may be inserted through a reduced size incision, due to the overall dimensions of device 100 being reduced during insertion.

Devices 100 of the disclosure enable a continuous expansion and distraction over a range of displacements according to predetermined dimensions of a specific spacer design. This provides the ability to distract vertebral bodies or other bones to a desired height or separation. Endplates 120, 122 can be shaped to form planes or surfaces which converge relative to each, to provide for proper lordosis, and can be provided with openings 134 through which bone ingrowth may grow, and into which bone graft material may be placed. Devices 100 of the disclosure may be used to distract, or force bones of a joint apart, or may be used to maintain a separation of bones created by other means, for example by a retractor. Endplates may additionally be curved to conform to the surface of body tissue, for example the surface of cortical bone, of the vertebra to be contacted, for improved fixation and load bearing.

Devices 100 of the disclosure may be further secured in connection with the body by passage of elongated fasteners through an endplate 120, 122. A blocking mechanism can be used to prevent backing out of an elongated fastener.

Devices 100 of the disclosure may be fabricated using any biocompatible materials known or hereinafter discovered, having sufficient strength, flexibility, resiliency, and durability for the patient, and for the term during which the device is to be implanted. Examples include but are not limited to metal, such as, for example titanium and chromium alloys; polymers, including for example, PEEK or ultra high molecular weight polyethylene (UHMWPE); and ceramics. There are many other biocompatible materials which may be used, including other plastics and metals, as well as fabrication using living or preserved tissue, including autograft, allograft, and xenograft material.

Portions or all of device 100 may be radiopaque or radiolucent, or materials having such properties may be added or incorporated into device 100 to improve imaging of the device during and after implantation.

Devices 100 may be formed using titanium, or a cobalt-chrome-molybdenum alloy, Co—Cr—Mo, for example as specified in ASTM F1537 (and ISO 5832-12). The smooth surfaces may be plasma sprayed with commercially pure titanium, as specified in ASTM F1580, F1978, F1147 and C-633 (and ISO 5832-2). Alternatively, part or all of devices 100 may be formed with a polymer, for example ultra-high molecular weight polyethylene, UHMWPE, for example as specified in ASTM F648 (and ISO 5834-2). In one embodiment, PEEK-OPTIMA (a trademark of Invibio Ltd Corp, United Kingdom) may be used for one or more components of devices 100 of the disclosure. For example, polymeric portions can be formed with PEEK-OPTIMA, which is radiolucent, whereby bony ingrowth may be observed. Other polymeric materials with suitable flexibility, durability, and biocompatibility may also be used.

In accordance with the invention, devices 100 of various sizes may be provided to best fit the anatomy of the patient. Components of matching or divergent sizes may be assembled during the implantation procedure by a medical practitioner as best meets the therapeutic needs of the patient, the assembly inserted within the body using an insertion tool. Devices 100 of the invention may also be provided with an overall angular geometry, for example an angular mating disposition of endplates, to provide for a natural lordosis, or a corrective lordosis, for example of from 0° to 12° for a cervical application, although much different values may be advantageous for other joints. Lordotic angles may also be formed by shaping one or both endplates to have relatively non-coplanar surfaces.

A kit can be provided which includes a plurality of either or both of endplates and bearings having differing lordotic profiles of uneven height along their length. The medical practitioner can select among the differing profiles to provide an optimal lordotic adjustment for the patient, the selection taking place during the surgical procedure.

Expanded implant heights, for use in the cervical vertebrae for example, may typically range from 7 mm to 12 mm, but may be larger or smaller, including as small as 5 mm, and as large as 16 mm, although the size is dependent on the patient, and the joint into which an implant of the invention is to be implanted. Devices 100 may be implanted within any level of the spine, and may also be implanted in other joints of the body, including joints of the hand, wrist, elbow, shoulder, hip, knee, ankle, or foot.

In accordance with the invention, a single device 100 may be used, to provide stabilization for a weakened joint or joint portion. Alternatively, a combination of two, three, or more of any of device 100 may be used, at a single joint level, or in multiple joints. Moreover, implants of the disclosure may be combined with other stabilizing means.

Additionally, devices 100 of the disclosure may be fabricated using material that biodegrades in the body during a therapeutically advantageous time interval, for example after sufficient bone ingrowth has taken place. Further, implants of the disclosure are advantageously provided with smooth and or rounded exterior surfaces, which reduce a potential for deleterious mechanical effects on neighboring tissues.

Any surface or component of a device 100 of the disclosure may be coated with or impregnated with therapeutic agents, including bone growth, healing, antimicrobial, or drug materials, which may be released at a therapeutic rate, using methods known to those skilled in the art.

Devices of the disclosure provide for adjacent vertebrae to be supported during flexion/extension, lateral bending, and axial rotation. In one embodiment, device 100 is indicated for spinal arthroplasty in treating skeletally mature patients with degenerative disc disease, primary or recurrent disc herniation, spinal stenosis, or spondylosis in the lumbosacral spine (LI-SI). Degenerative disc disease is advantageously defined as discogenic back pain with degeneration of the disc confirmed by patient history and radiographic studies, with or without leg (radicular) pain. Patients are advantageously treated, for example, who may have spondylolisthesis up to Grade 1 at the involved level. The surgery position device 100 may be performed through an Anterior, Anterolateral, Posterolateral, Lateral, or any other approach.

In a typical embodiment, devices 100 of the disclosure have an uncompressed height, before insertion, of 7 to 13 mm, and may advantageously be provided in cross-sections of 8×22, 8×26, 8×30, 8×34, 10×27 mm, 12×32 mm and 12×37 mm, and can optionally be provided with 4, 8, 12, 15, 20, 25, or 30 degree lordotic angles, although these are only representative sizes, and substantially smaller or larger sizes can be therapeutically beneficial. In one embodiment implants in accordance with the instant disclosure are sized to be inserted using an MIS approach, for example using a reduced incision size, for example less than about 5 cm, and advantageously less than about 1 cm, with fewer and shorter cuts through body tissue. Device 100 may advantageously be used in combination with other known or hereinafter developed forms of stabilization or fixation, including for example rods and plates, or intradiscal fixation, potentially connecting device 100 to one or more of the adjacent vertebrae.

Devices 100 of the disclosure can be inserted into the body, advantageously in a contracted or non-expanded configuration, through a transforaminal approach, and can be positioned in attachment to an inserter tool, for example as shown in FIGS. 18-21, or by using another tool, for example for anterior placement. Once placement is achieved, device 100 is capable of expanding for disc height restoration. To maintain an engagement device 100 and an insertion tool, a driving end (not shown) of the tool can be engaged with device 100, for example by a threaded coupling.

All references cited herein are expressly incorporated by reference in their entirety. There are many different features of the present disclosure and it is contemplated that these features may be used together or separately. Unless mention was made above to the contrary, it should be noted that all of the accompanying drawings are not to scale. Thus, the disclosure should not be limited to any particular combination of features or to a particular application of the disclosure. Further, it should be understood that variations and modifications within scope of the disclosure might occur to those skilled in the art to which the disclosure pertains. Accordingly, all expedient modifications readily attainable by one versed in the art from the disclosure set forth herein that are within the scope of the present disclosure are to be included as further embodiments of the present disclosure.

What is claimed is:

1. A method for stabilizing bones comprising:
providing a device for separating bones of a joint using a driver tool having a threaded shaft, the spacer having:
a superior endplate having a bone engaging surface and a surface opposite the bone engaging surface, and ramps including at least two inferior facing ramps;
an inferior endplate having a bone engaging surface and a surface opposite the bone engaging surface, and ramps including at least two superior facing ramps;
first and second bearings disposed between the first and second endplates, each having ramps including at least one superior facing ramp mateably engaged with an inferior facing ramp of the superior endplate, and at least one inferior facing ramp mateably engaged with a superior facing ramp of the inferior endplate,
the first bearing including a threaded aperture, the second bearing including a thrust surface, the threaded aperture threadably engageable with the threaded shaft of the driver tool,
the thrust surface aligned with the threaded shaft to be pushable by the threaded shaft when the threaded shaft is threaded through the threaded aperture to thereby cause the first and second bearings to be driven apart, whereby the ramps of the first and second bearings bear against the ramps of the superior endplate and the ramps of the inferior endplate to thereby push the superior endplate away from the inferior endplate,
wherein the threaded aperture is disposed at a non-orthogonal angle with respect to a longitudinal axis of the device, and
positioning the spacer between adjacent bones using a lateral approach.

2. The method of claim 1, wherein positioning the spacer includes inserting the spacer in an unexpanded state through an opening in Kambin's triangle.

3. The method of claim 1, the ramps of the first and second bearings and the at least two ramps of the superior endplate and the at least two ramps of the inferior endplate are oriented at a non-orthogonal angle with respect to a longitudinal axis of the device.

4. The method of claim 1, wherein the first and second bearings are displaced relative to each other along the longitudinal axis of the device when the first and second bearings are pushed apart by the driver.

5. The method of claim 1, further including the threaded driver.

6. The method of claim 5, wherein the driver includes a threaded end and a handle, the threaded end separable from the handle, whereby the threaded end can remain with the device within the body.

7. The method of claim 1, a leading end of at least one of the superior endplate and the inferior endplate provided with an angular profile, whereby a leading end of the device has a tapering leading end profile.

8. The method of claim 7, the threaded aperture forming an acute angle with respect to a longitudinal axis of the device which opens in a direction away from the leading end.

9. The method of claim 8, whereby the device includes no more than 5 parts, limited to the superior and inferior endplates, the first and second bearings, and the threaded shaft.

10. The method of claim 1, further including a radiopaque material.

11. The method of claim 1, the superior and inferior endplates, and the first and second bearings all mutually nesting when the device is in a collapsed configuration to thereby present a reduced radial profile to facilitate insertion of the device into a patient.

12. The method of claim 1, ramps of the bearings being at least one of recessed relative to a surrounding surface and projecting relative to a surrounding surface, wherein when a mating ramp of the superior endplate and a mating ramp of the inferior endplate are mated to a recessed bearing ramp, the mating ramp is projecting relative to a surrounding surface, and when a mating ramp of the superior endplate and a mating ramp of the inferior endplate are mated to a projecting bearing ramp, the mating ramp is recessed relative to a surrounding surface.

13. A method for stabilizing bones comprising:
providing a spacer having:
a superior endplate having a bone engaging surface and a surface opposite the bone engaging surface, and ramps including at least two inferior facing ramps;
an inferior endplate having a bone engaging surface and a surface opposite the bone engaging surface, and ramps including at least two superior facing ramps;
first and second bearings disposed between the first and second endplates, each having ramps including at least one superior facing ramp mateably engaged with an inferior facing ramp of the superior endplate, and at least one inferior facing ramp mateably engaged with a superior facing ramp of the inferior endplate,
the first bearing including a threaded aperture, the threaded aperture threadably engageable with a driver tool, wherein the threaded aperture is disposed at a non-orthogonal angle with respect to a longitudinal axis of the device,
positioning the spacer between adjacent bones using a lateral approach;
rotating the driver tool to push the inferior endplate away from the superior endplate to restore a therapeutic alignment of the bones of the joint;
removing the driver tool to leave the threaded shaft within the device
wherein the spacer includes opening to an interior of the spacer, the method further including inserting a bone growth material into the opening of an expanded spacer.

14. The method of claim 13, wherein positioning the spacer includes inserting the spacer in an unexpanded state through an opening in Kambin's triangle.

15. The method of claim 13, wherein inserting a bone growth material includes inserting at least one of an autograft, allograft, xenograft, and bone substitute.

\* \* \* \* \*